United States Patent
Osipchuk et al.

(10) Patent No.: US 6,899,800 B2
(45) Date of Patent: May 31, 2005

(54) POLYMERIC ELECTRODE FOR ELECTROPHYSIOLOGICAL TESTING

(75) Inventors: Yuri Osipchuk, Foster City, CA (US); Alexei Savtchenko, Palo Alto, CA (US); Alexander A. Dromaretsky, Irvine, CA (US)

(73) Assignee: Axon Instruments, Inc., Union City, CA (US)

( * ) Notice: Subject to any disclaimer, the term of this patent is extended or adjusted under 35 U.S.C. 154(b) by 344 days.

(21) Appl. No.: 10/176,183

(22) Filed: Jun. 20, 2002

(65) Prior Publication Data

US 2002/0195337 A1 Dec. 26, 2002

Related U.S. Application Data

(60) Provisional application No. 60/299,675, filed on Jun. 20, 2001.

(51) Int. Cl.$^7$ ............................ G01N 27/327; C12M 1/34; C12N 13/00
(52) U.S. Cl. ............................ 204/403.01; 204/297.1; 435/173.4; 435/287.1
(58) Field of Search ............................ 204/297.1, 403.01; 435/173.4–176, 287.1

(56) References Cited

U.S. PATENT DOCUMENTS 5,799,151 A * 8/1998 Hoffer .................... 709/204
5,823,428 A * 10/1998 Humberstone et al. ......... 239/4
6,315,940 B1 * 11/2001 Nisch et al. .............. 435/287.1

FOREIGN PATENT DOCUMENTS

WO    WO 01/25769 A2    4/2001    .......... G01N/27/00

OTHER PUBLICATIONS

Kostyuk et al. ("Effect of internal fluoride and phosphate on membrane currents during intracellular dialysis of nerve cells," Nature vol. 257, Oct. 23, 1975).*

* cited by examiner

Primary Examiner—Alex Noguerola
(74) Attorney, Agent, or Firm—Antonio R. Durando; Quarles & Brady Streich Lang LLP (57) ABSTRACT

A polymeric material such as PDMS is molded into an electrode structure containing a micron-size aperture for receiving and forming a giga-ohm seal with a biological membrane. One end of a tube is filled with uncured polymeric material and pressed against a support surface to prevent drainage. A conventional micropipette having a size suitable for sliding through the tube is introduced, tip first, into the tube and is allowed to fall through the polymeric material and rest against the support surface. The assembly is heated to cure the polymer and the micropipette is removed from the tube, thereby leaving a polymeric plug at the end of the tube with an aperture suitable in shape and size for patch-clamp giga-ohm seal electrode applications. A multi-well tray with a polymeric electrode plug in each well is constructed using the same approach.

9 Claims, 12 Drawing Sheets

POLYMERIC ELECTRODE FOR ELECTROPHYSIOLOGICAL TESTING

RELATED APPLICATIONS

This application is based on U.S. Provisional Application Ser. No. 60/299,675, filed on Jun. 20, 2001.

BACKGROUND OF THE INVENTION

1. Field of the Invention

This invention is related in general to patch-clamp electrodes for electrophysiological testing of cells. In particular, the invention concerns a method for the manufacture of poly-dimethylsiloxane (PDMS) electrodes capable of forming high electrical resistance patch clamp recordings suitable for measurements in automated, repeatable, parallel experiments.

2. Description of the Related Art

Conventional voltage clamping techniques used to conduct electrophysiological tests on a membrane assess electrical activity on the membrane by measuring current or voltage changes produced in response to exposure to various test stimuli. Typically, the membrane is pierced with two microelectrodes connected to an amplifier capable of recording current or voltage variations in response to stimuli such as voltage step changes, the application of compounds, or mechanical stimulation.

Similarly, using patch clamping techniques, the membrane potential can be held constant while the current flowing through the membrane is measured to detect ion-channel activity that corresponds to changes in the membrane's conductance. Instead of using sharp microelectrodes to puncture the membrane and penetrate the cell, like in traditional voltage clamping, patch clamping uses a micropipette with a heat-polished tip of about 1 to 5 micron in diameter that is physically sealed to a "patch" on the membrane. The same pipette is used continuously for both current passing and voltage recording. For the most part, patch clamping is used either with a whole-cell or a single-channel mode of operation. In whole-cell patch clamping, the membrane at the tip of the pipette is ruptured to produce electrical continuity between the electrolyte in the pipette and the interior of the cell. Thus, total membrane current or voltage is measured. In single-channel patch clamping, the integrity of the membrane at the tip of the pipette is preserved. Accordingly, the recorded current is only the current flowing through the patch of the membrane enclosed by the tip of the pipette. Since this area is very small, there is a good chance that only one or a small number of ion channels may be in the membrane patch, and individual ion-channel currents may be recorded.

In both types of patch-clamp techniques, when the tip of the pipette is pressed against the cell membrane, the interior of the pipette is isolated from the extracellular solution by the seal that is formed between the tip of the pipette and the membrane. If the electrical resistance of the seal is sufficiently large, negligible current can leak across the seal and good measurements are obtained. Thus, any leakage of current through the seal is undesirable and the creation of a high-resistance seal (in the order of giga-ohms) is crucial for good results.

Figure 1:
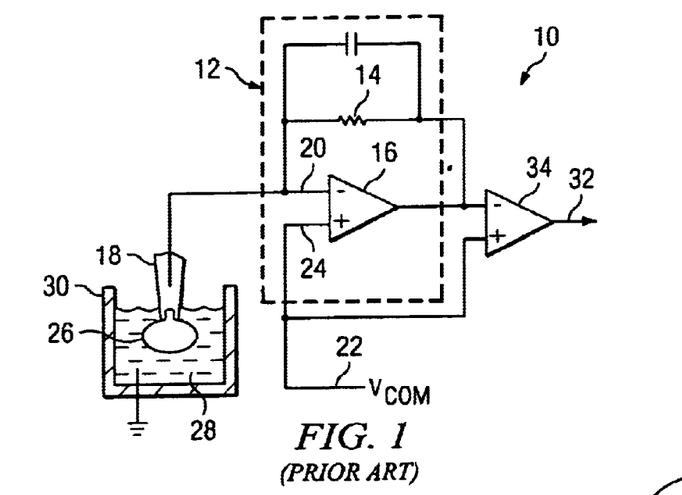
FIG. 1 is a schematic diagram of a conventional patch-clamp circuit applied to a cell in a test chamber.
Figure 2A:
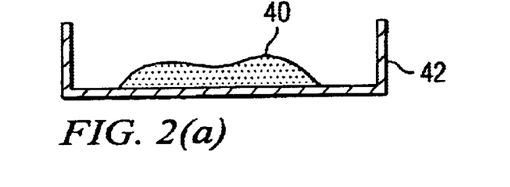
FIGS. 2(a)–(f) are schematic illustrations of the steps and apparatus required to practice the invention in its simplest form.
Figure 2B:
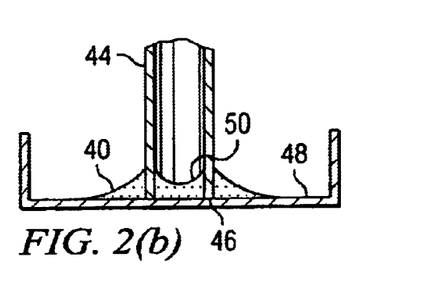
Figure 2C:
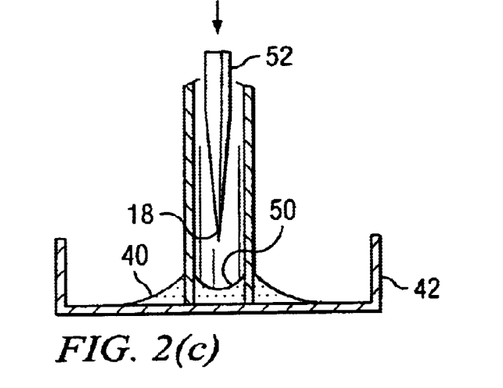
Figure 2D:
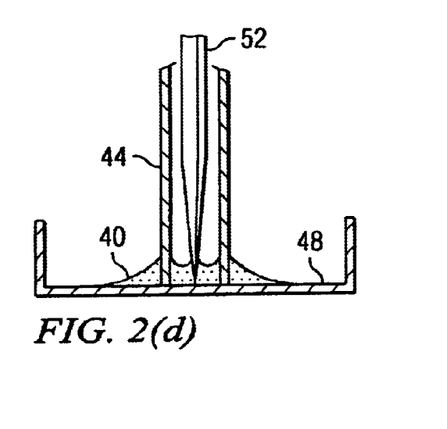
Figure 2E:
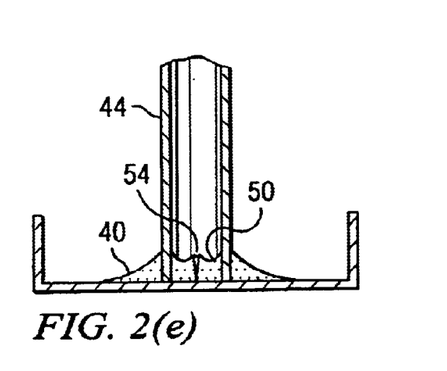
Figure 2F:
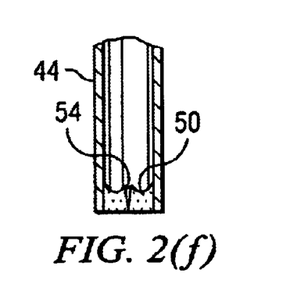

The basic design of a patch-clamp circuit 10 is illustrated in FIG. 1. A sensitive current-to-voltage converter 12 is fabricated using a high-megaohm (or giga-ohm, used for single-channel recordings) resistor 14 and an operational amplifier 16. A patch-clamp micropipette (only the tip 18 is shown) is connected to the negative input 20 and the control voltage 22 (Vcom) to the positive input 24 of the operational amplifier 16. The tip 18 of the pipette is adhered to the membrane of a test cell 26 immersed in a grounded electrophysiological bath 28 in a test chamber 30, such as to form a seal between the cell membrane and the glass pipette tip. Since the operational amplifier 16 has extremely high gain, the potential at the negative input 20 is forced to follow the potential Vcom established at the positive input 24. All current flowing in the micropipette also flows through the resistor 14. This current is proportional to the voltage across the resistor 14, and it is measured at the output 32 of the differential amplifier 34.

In order to improve the seal resistance for patch-clamp recordings, investigators have focussed on processes for improving the adhesion of conventional glass and quartz pipettes to the biological membrane. For example, Kiminori (Japanese Publication No. 4338240) taught that plasma treatment of the glass tip of a conventional micropipette improves the patch-clamp seal. New materials and patch-clamp seal geometries have also been investigated. For instance, Cytion's International Application No. PCT/IB98/01150 describes a perforated partition with multiple holes to form a plurality of patch-clamp seals between intra and extracellular compartments. In particular, K. G. Klemic et al. of Yale University have discovered that an electrode formed with silicone polymers (especially PDMS), in the form of a planar partition with multiple openings, is particularly suitable for producing giga-ohm patch-clamp seals with cell membranes.

The efficient construction of such a partition with apertures capable of providing effective patch clamps in repeatable and durable implementation remains a challenge in the art. This invention is directed at a simple and very effective process for manufacturing such a polymeric patch-clamp electrode.

BRIEF SUMMARY OF THE INVENTION

The primary objective of this invention is a polymeric patch-clamp electrode capable of forming a giga-ohm seal with a biological membrane.

Another objective of the invention is a method of manufacture of such polymeric patch-clamp electrodes in a form suitable for the sequential testing of animal cells through successive exposures to multiple perfusion solutions in an automated, continuous, high-throughput system.

In particular, a goal of the invention is a patch-clamp electrode made of PDMS and a method of forming a PDMS multi-well structure with consistent geometry and sealing properties.

Another object is a simple and reliable process for manufacturing a patch-clamp electrode from a curable polymer such as PDMS.

Still another objective is a method of manufacture that can be adapted for making trays of multi-well patch-clamp electrodes for parallel testing of multiple cells in a high-throughput testing system.

Another goal is a patch-clamp electrode design that is suitable for implementation within an overall automated patch-clamp and solution-delivery system.

Yet another object is a system that can be implemented using conventional patch-clamp electronic hardware and software, modified only to the extent necessary to meet the design parameters of the polymeric electrode of the invention.

A final objective is a system that can be implemented economically according to the above stated criteria.

Therefore, according to these and other objectives, the present invention consists of molding a polymeric material such as PDMS into a structure containing a micron-size aperture for receiving and forming a giga-ohm seal with a biological membrane. In its simplest form, the invention consists of filling a few millimeters of one end of a tube with a selected, uncured, polymeric material and pressing it against a support surface to prevent the drainage of the liquid material from the tube. A conventional micropipette having a size suitable for sliding through the tube is introduced, tip first, into the tube and is allowed to fall, penetrate the polymeric material, and naturally rest against the support surface. The assembly of these components is heated for a predetermined period of time to cure the polymer, and the micropipette is then removed from the tube, thereby leaving a polymeric plug formed at the end of the tube with an aperture suitable in shape and size for use in a patch-clamp electrode. Accordingly, the tube may be used advantageously in a conventional patch-clamp well to form a giga-ohm seal with a cell drawn to the aperture in the polymeric plug.

According to one aspect of the invention, the geometry of a micropipette tip used for conventional patch clamping is utilized to produce the proper shape for similar giga-ohm seal applications with a polymeric electrode. Since the aperture formed in the cured polymeric structure is determined by the shape of the tip of the micropipette used in the process of manufacture, it follows that the resulting polymeric structure corresponds to the micropipette and is equivalently suitable for patch-clamp applications.

According to another aspect of the invention, tubes and corresponding micropipettes are combined to obtain multiple sets of guide-tube/plunger molding assemblies used to produce a plurality of polymeric plugs automatically in a multi-well tray for parallel patch-clamp testing of animal cells. A rigid tray is provided with a plurality of wells, where each well contains a perforation a few millimeters deep for receiving a polymeric plug according to the invention. Each perforation is further adapted to mate with a support assembly on one side and with a molding assembly on the other. Each support assembly consists of a removable plunger with a top surface that is capable of sealingly mating with the bottom side of the perforation in a well and that is shaped to define the configuration of the polymeric aperture produced according to the invention. Each molding assembly consists of an outer sleeve capable of sealingly mating with the top side of the perforation in a well and an inner pointed plunger with a tip sized to produce the desired patch-clamp electrode aperture. Each support assembly and molding assembly is mounted on a corresponding support frame parallel to the multi-well tray and in alignment with the well perforation, such that they can be combined with or removed from the multi-well tray as separate manufacturing components.

The top surface of each support assembly is covered with an appropriate amount of liquid polymeric material and all support assemblies are raised as a unit to engage the bottom side of each perforation in the multi-well tray, thereby forcing the liquid material into the perforation. Alternatively, the support assemblies are first raised to engage the bottom side of the multi-well tray and then covered with an appropriate amount of liquid polymeric material by injecting it into the perforations of the tray. The molding assemblies are then lowered as a unit to seal the top of each well, and the plungers are released to penetrate the perforation in each well and contact the top surface of a corresponding support assembly through the polymeric material, thereby molding the patch-clamp electrode aperture in the liquid material. The entire assembly is then treated as needed to cure the polymeric material. Finally, the plungers are removed from the cured polymer plugs formed in the wells' perforations, and the support assembly and molding assemblies are separated from the tray. The resulting product is a multi-well tray with a polymeric plug in each well that contains an aperture suitable for giga-ohm patch-clamp testing.

Because the multi-well trays of the invention can be used in a fully automated environment, they are suitable for use in multi-chamber parallel-testing systems wherein each chamber is used sequentially or in parallel to test cells with a variety of perfusion solutions. Multiple perfusion chambers equipped with the electrode trays of the invention can be operated independently and in parallel with greatly reduced manual operation. In essence, operator intervention is only required, at the most, for changing trays and for maintenance when these steps are not also automated. Therefore, series of successive tests can be carried out rapidly and precisely.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

BRIEF DESCRIPTION OF THE DRAWINGS

FIGS. 13(*a*)–(*d*) illustrate another embodiment of the invention wherein polymeric electrode plugs are formed within cavities in a layer of the same polymeric material.

DESCRIPTION OF THE PREFERRED EMBODIMENTS OF THE INVENTION

This invention lies in the recognition that a conventional patch-clamp micropipette provides an optimal design for molding polymeric materials into electrode partitions capable of giga-ohm seals. Accordingly, all embodiments of the invention are based on the idea of using the tip of a conventional micropipette, or an equivalent structure, as a molding tool immersed in polymeric material to form a patch-clamp electrode structure.

A patch-clamp micropipette is an electrode component obtained by pulling a heated glass tube (1.0–2.0 micron OD) to form a pointed end with a very fine tip (in the order of 1–10 microns ID opening) that breaks off under the applied tensile force. Such micropipettes have been used for decades and are well known and defined in the art of electrophysiology. Therefore, they are not further described for the purpose of this disclosure.

Referring to the figures, wherein the same reference numerals and symbols are used throughout for like parts, FIG. 2(*a*)–2(*f*) are schematic illustrations of the steps and apparatus used to practice the simplest embodiment of the invention. A small amount (e.g., 50–200 $\mu$l, typically 100 $\mu$l) of a liquid polymeric material, such as newly mixed PDMS components, is placed into a container 42, such as a plastic petri dish, to form a puddle 40 [FIG. 2(*a*)]. (As is well known in the art, PDMS is made according to specifications given by various manufacturers, such as G.E. Silicones and Dow Corning.) A relatively large (e.g., about 1.8 mm OD) ordinary tube 44 is lowered through the PDMS puddle 40 and pressed down with sufficient constant force to keep the end 46 of the tube in contact with the bottom 48 of the container and isolate a PDMS plug 50 within the tube 44 [FIG. 2(*b*)]. A conventional patch-clamp pipette 52 with outside diameter slightly smaller than the inside diameter of the tube 44 is gently inserted into the tube 44 and dropped (from a few millimeters above the PDMS plug 50), so that it can slide by gravity inside the tube 44 [FIG. 2(*c*)]. Simply as a result of gravity, the tip 18 of the pipette 52 will pierce through the liquid PDMS and rest against the bottom 48 of the container 42, thereby displacing liquid material to form an opening in the plug 50, as illustrated in FIG. 2(*d*). The resilience of any material constituting the bottom 48 of the container 42 (preferably plastic, but glass and even metals have been found to be adequate) is sufficient to form a complete connection with the tip 18 of the pipette because of the relatively very high pressure resulting from its very small area of contact. The polymeric material is then allowed to polymerize, as needed (PDMS is best cured in an oven for about 20 minutes at about 80° C.). The inner pipette 52 is then lifted from the PDMS material, leaving a molded plug 50 with an aperture 54 sized and shaped by the tip 18 of the patch-clamp pipette 52 [FIG. 2(*e*)]. The tube 44 with the perforated PDMS plug 50 illustrated in FIG. 2(*f*) provides an electrode structure suitable for a giga-ohm seal patch-clamp applications.

Figure 3:
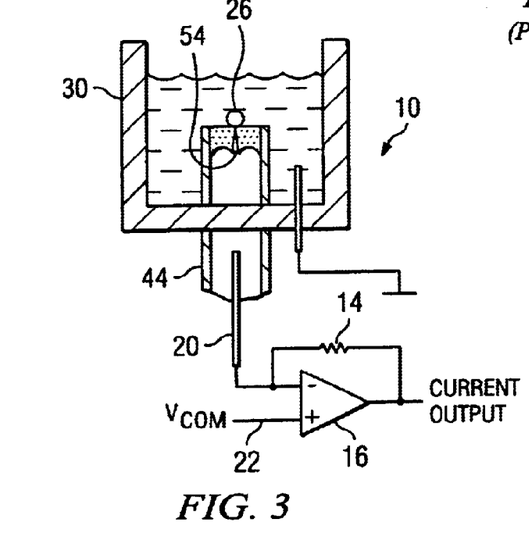
FIG. 3 is a schematic diagram of the electrode of the invention utilized in a simplified conventional patch-clamp set-up.

As shown in FIG. 3, the tube 44 of FIG. 2(*f*) can be used to form the electrode of a conventional patch-clamp setup. After plasma treatment to improve its seal-forming characteristics, the tube 44 is inserted (shown up-side-down) in a recording chamber 30 and connected to the patch-clamp circuit 10 of FIG. 1. A test cell 26 is drawn to the aperture 54 to form a seal in the same way the tip 18 of a micropipette 52 has been used in the prior art. Using a PDMS plug 50 with an aperture 54 about 2 microns in diameter at the tip (where it initially contacts the cell), we found that the patch-clamp operation was quite simple and straightforward, and it produced a giga-ohm seal.

Figure 4:
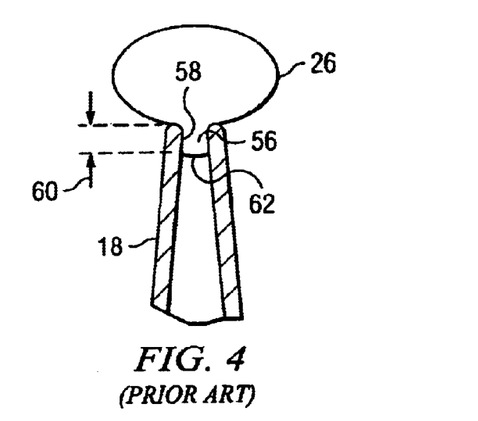
FIG. 4 is a partially sectioned, greatly enlarged, view of the tip of a conventional patch-clamp micropipette after engagement of a cell membrane to form a high-resistance seal.

In the art of patch-clamp electrophysiology, it is well known that best patch-clamp seals are obtained when the contact between the membrane of the cell being tested and the tip of the micropipette is extended over an overlapping region of a few microns. As illustrated in partial cross-section in FIG. 4, the seal is formed by applying a vacuum to the micropipette, which partly draws the cell 26 into the tip 18 of the pipette. Thus, a portion 56 of cell membrane conforms to the interior surface of the tip 18 and produces a corresponding annular envelope 58 of contact surface that greatly enhances the resistance of the seal. For best results, it has been estimated that the height 60 of the envelope 58 should be in the 4–6 micron range. Note that the same criterion applies for whole-cell applications, where the innermost portion 62 of the membrane is ruptured, as for single-channel operation.

In view of the foregoing, the preferred embodiment of the plug 50 of the invention is approximately 1–2 mm high and has a correspondingly long tapered aperture 54 with a diameter of about 0.5–20 microns at its smaller end, as determined by the size of the micropipette used to mold it. The diameter of the plug 50, which is determined by the inside diameter of the outer tube 44, is typically about 1.0–1.3 mm. It is noted that the tube 44 and the patch-clamp pipette 52 (or equivalent structures used to form the plug 50 according to the invention) are preferably selected so that the inner pipette 52 can fall freely as a plunger through the outer tube 44 simply as a result of gravity. To that end, a free space of about 50 microns on each side of the inner pipette 44 provides sufficient room for the gas trapped at the bottom of the outer tube 44 to escape upwards and allow the free fall of the tip 18 into the plug 50 in its liquid state. Because of its extremely small size (in the order of a few microns), the tip 18 is able to penetrate the polymeric layer and exert sufficient pressure on the surface of the structure supporting it to completely cut through the liquid layer to form the aperture 54.

Figure 5A:
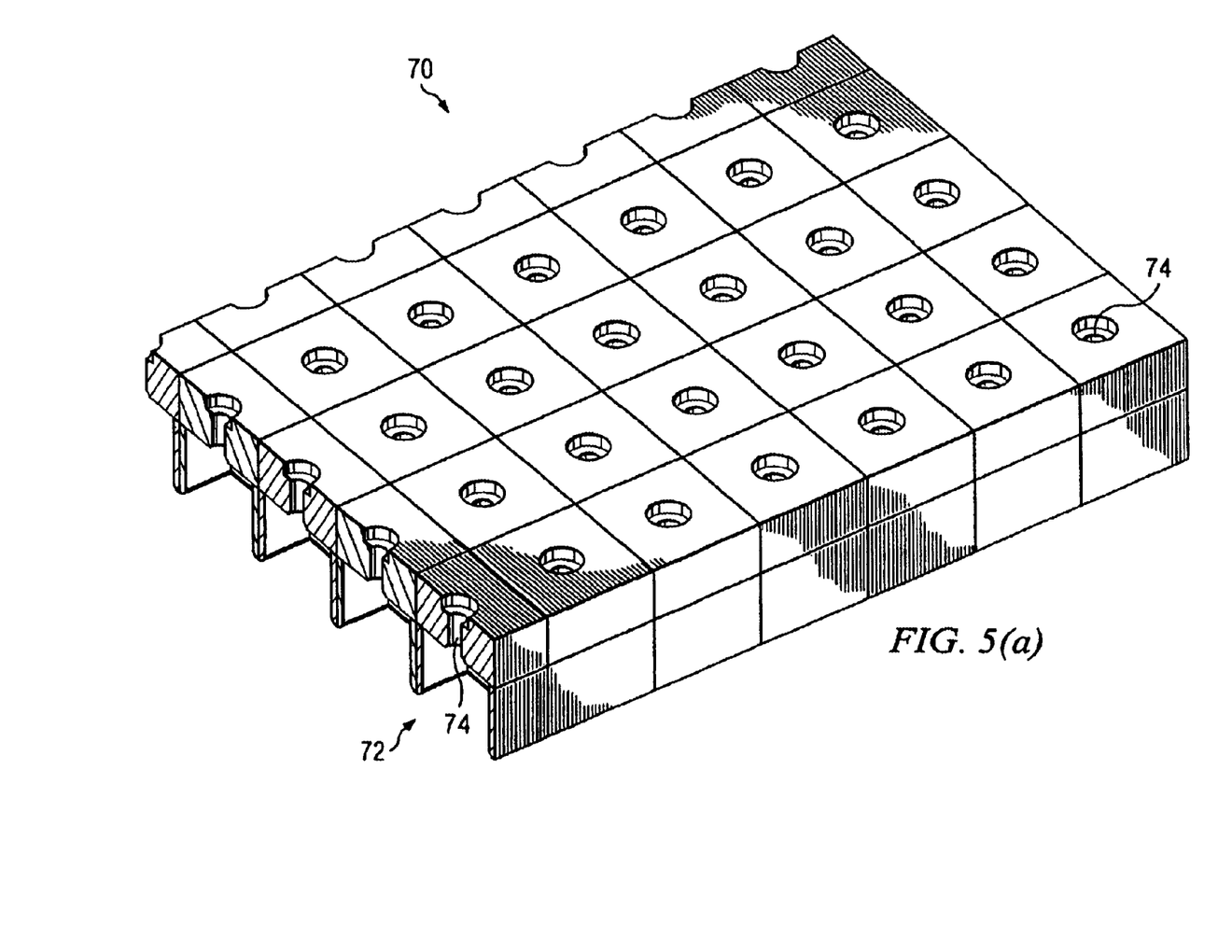
FIGS. 5(a) and 5(b) are partially sectioned perspective views of the top and bottom sides, respectively, of a plastic structure used to manufacture a multi-well tray with polymeric plugs made according to the present invention.
Figure 5B:
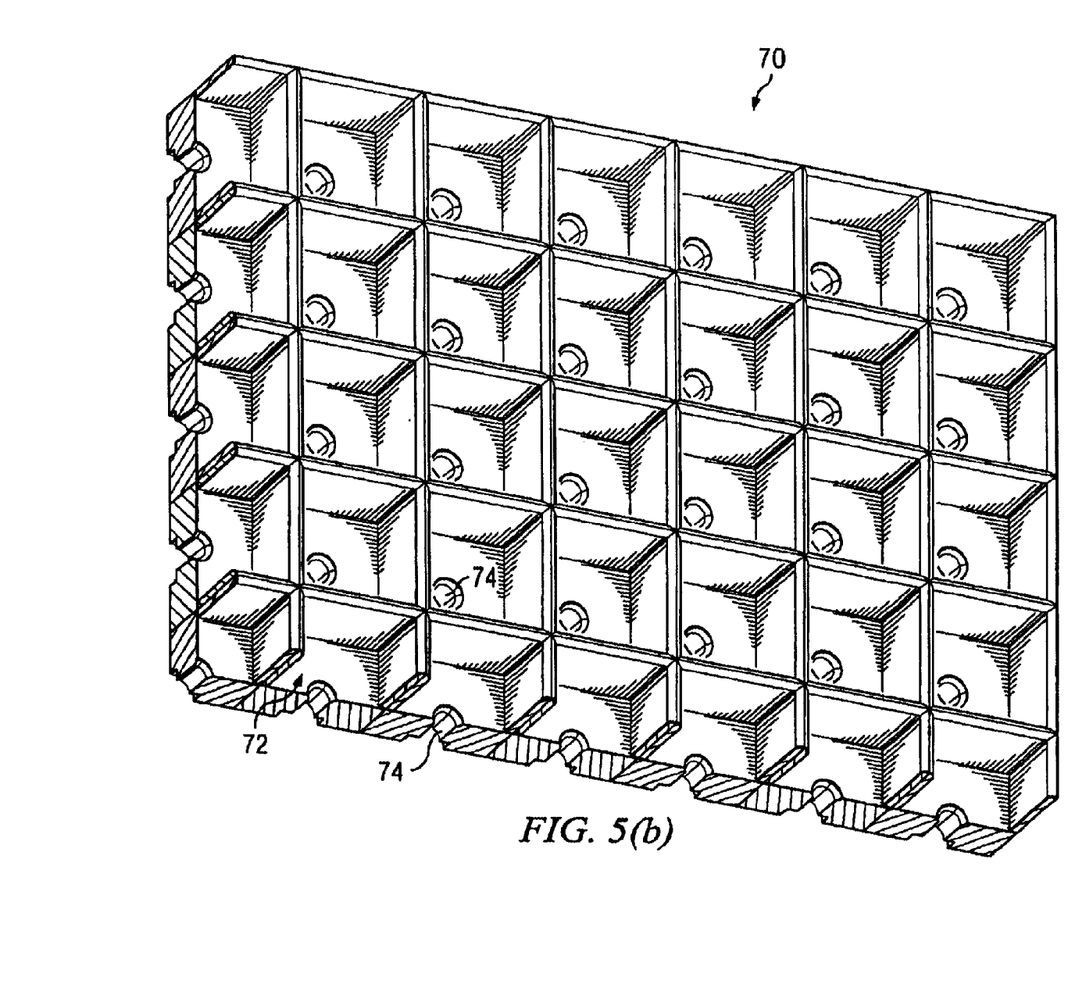
Figure 6:
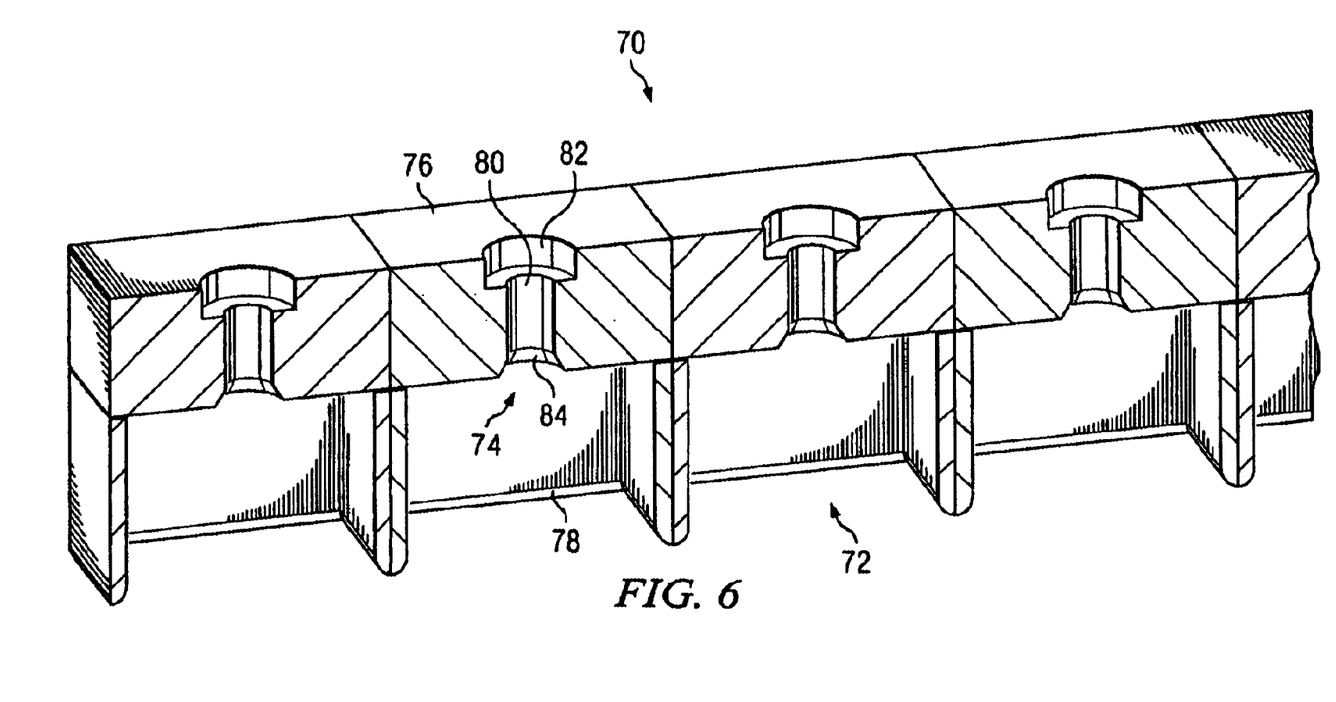
FIG. 6 is a cross-section of the tray of FIG. 5, shown up-side-down for convenience to illustrate the process of manufacture of a multi-well tray containing polymeric electrode plugs according to the invention.

The concept of the invention has been extended to an automated system for producing multiwell trays for parallel patch-clamp measurements of cell membranes wherein each well contains a polymeric plug formed as described above. The manufacture process is carried out by providing a rigid tray substrate 70 with a plurality of wells 72, as illustrated in FIGS. 5(*a*) and 5(*b*) (top and bottom views, respectively); for example, a 16×24 matrix of 384 wells may be disposed in rows and columns in a form suitable for incorporation with automated perfusion and recording equipment. As also seen in the cross-sectional view of FIG. 6, wherein the tray substrate 70 is shown up-side-down for convenience in describing the process of manufacture, each well 72 includes at least one through perforation 74 connecting the electrode side 76 to the perfusion side 78 of the well. Each perforation has a mid-portion 80 that is intended to receive a polymeric plug 50 manufactured according to the invention. Accordingly, the portion 80 is preferably at least 0.1 mm deep (typical range is 0.1–5.0 mm). A separate, electrode-side portion 82 of each perforation 74 consists of an enlarged, preferably cylindrical cavity adapted to receive a molding assembly lowered from above to mate in sealed engagement with the perforation 74. Similarly, the perfusion-side portion 84 of each perforation 74 is preferably tapered to receive a support assembly raised from below to mate in sealed engagement therewith.

Figure 7:
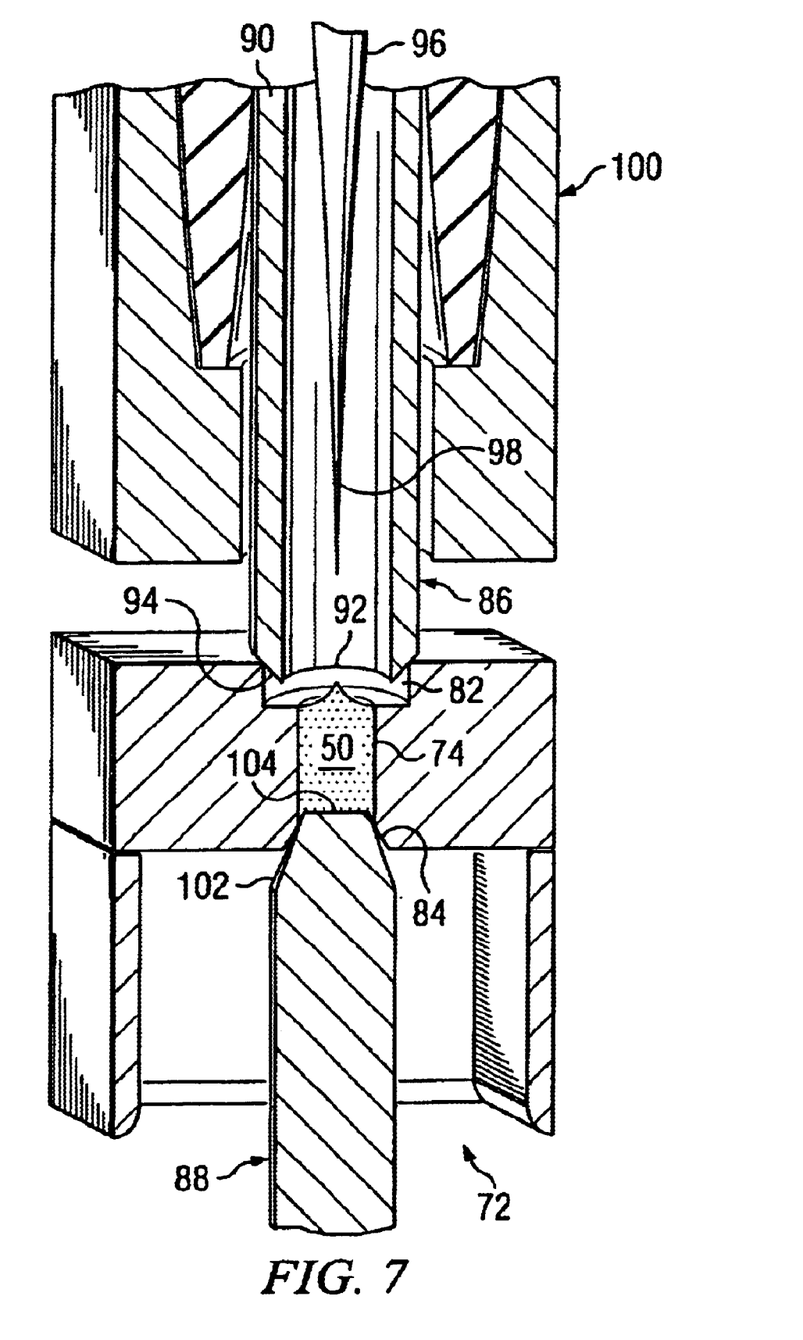
FIG. 7 is an enlarged cross-sectional view of a single well in FIG. 6 after engagement of the well perforation with a molding assembly from above and a support assembly from below.

Referring to FIG. 7, a single well perforation 74 is illustrated in an enlarged cross-sectional view after engagement of the well perforation by a molding assembly 86 from above and a support assembly 88 from below. The operation is illustrated with respect to a single well for convenience, but it is understood that it can be performed simultaneously in each well with robotic equipment. The molding assembly comprises a sleeve 90 (equivalent to the tube 44 of FIG. 2) with a tip 92 adapted for establishing a sealed connection with the electrode-side cavity 82 of the perforation 74. This sealed connection is preferably obtained through a self-aligning beveled surface 94 engaged by the rim of the cavity 82 as the assembly 86 is lowered. The molding assembly further includes a pointed inner plunger 96 (equivalent to the patch-clamp pipette 52 of FIG. 2) with a tip 98 sized to produce the desired aperture 54 (see FIG. 2) in the polymeric plugs to be formed according to the invention. The molding assembly 86 is mounted in a support structure 100 adapted for repeatedly lowering and raising the assembly 86 in alignment with the perforation 74.

Similarly, the perfusion-side portion 84 of the perforation 74 is plugged from below by a support assembly 88, which consists of a finger with a tapered end 102 sized to mate with the tapered portion 84 of the perforation. Prior to being raised to meet the well perforation 74, the top surface 104 of the finger 88 is covered with an appropriate amount of polymeric material to approximately fill the mid-portion 80 of the through perforation 74. Thus, the material required to form an electrode plug 50 according to the invention is put in place by raising the support assembly 88 into the perforation 74, as illustrated in FIG. 7. Again, alternatively, the fingers 88 could be first raised to meet the well perforations 74 and then covered with the appropriate amount of polymeric material.

Figure 8:
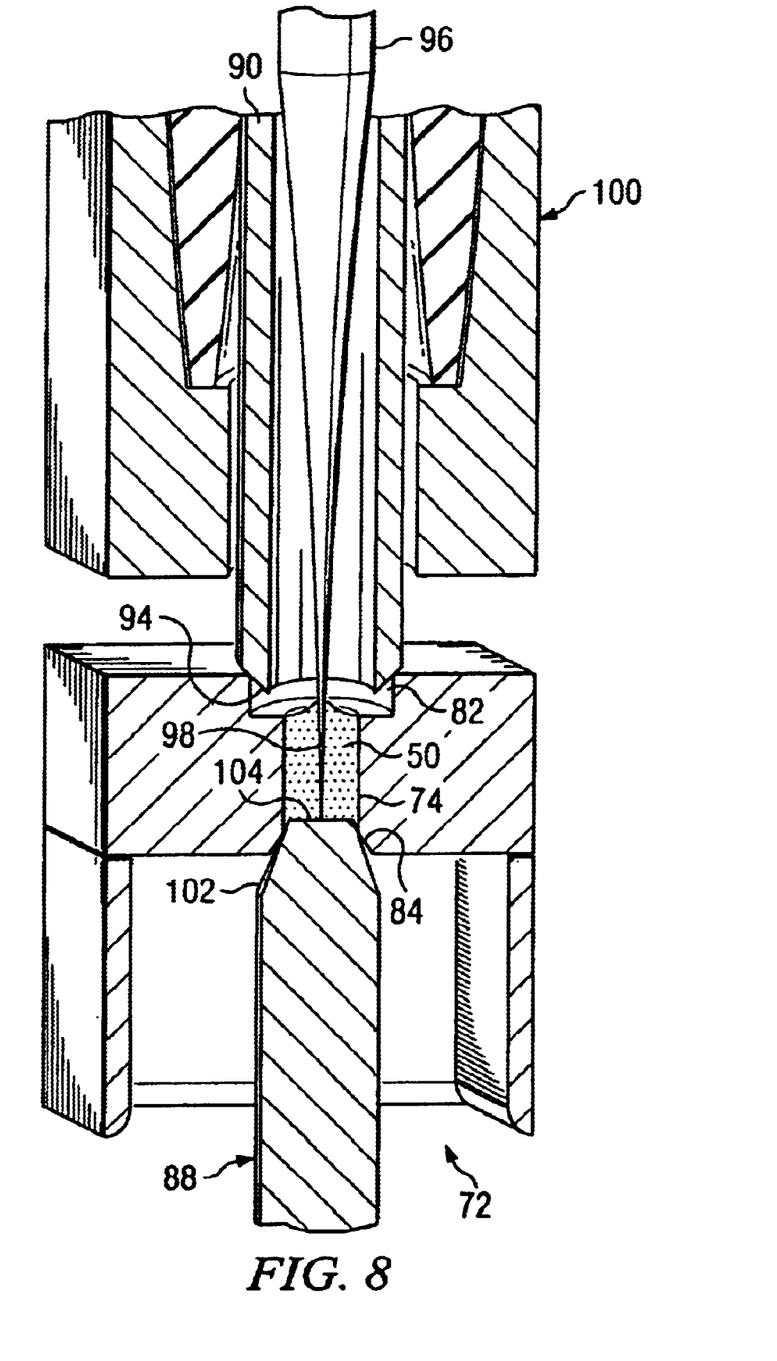
FIG. 8 shows the pointed plunger of the molding assembly after it has been lowered to pierce the uncured polymeric layer resting in the perforation in a well of a multi-well tray substrate.

The pointed plunger 96 of the molding assembly 86 is then lowered through the sleeve 90 to pierce the polymeric plug 50 lodged in the mid-portion 80 of the perforation 74 and firmly rest, preferably by gravity, on the top surface 104 of the finger 88, as illustrated in FIG. 8, thereby molding a patch-clamp aperture 54 according to the invention. In order to facilitate the contact between the plunger's tip 98 and the surface 104, the tapered end 102 of the finger 88 is preferably made of plastic material, though it could be made of glass, metal, or any other material capable of conforming to microscopic imperfections in the surface 104. After curing of the polymeric material, the tip 98 of the plunger 96 in the molding assembly is removed from the solid polymeric plug 50 and the aperture 54 is cleared. Finally, the support assembly 88 is lowered and the molding assembly 86 is raised from the tray substrate 70, so that the multi-well structure 70 is released with a ready-for-use perforated electrode plug 50 in each well.

Figure 9:
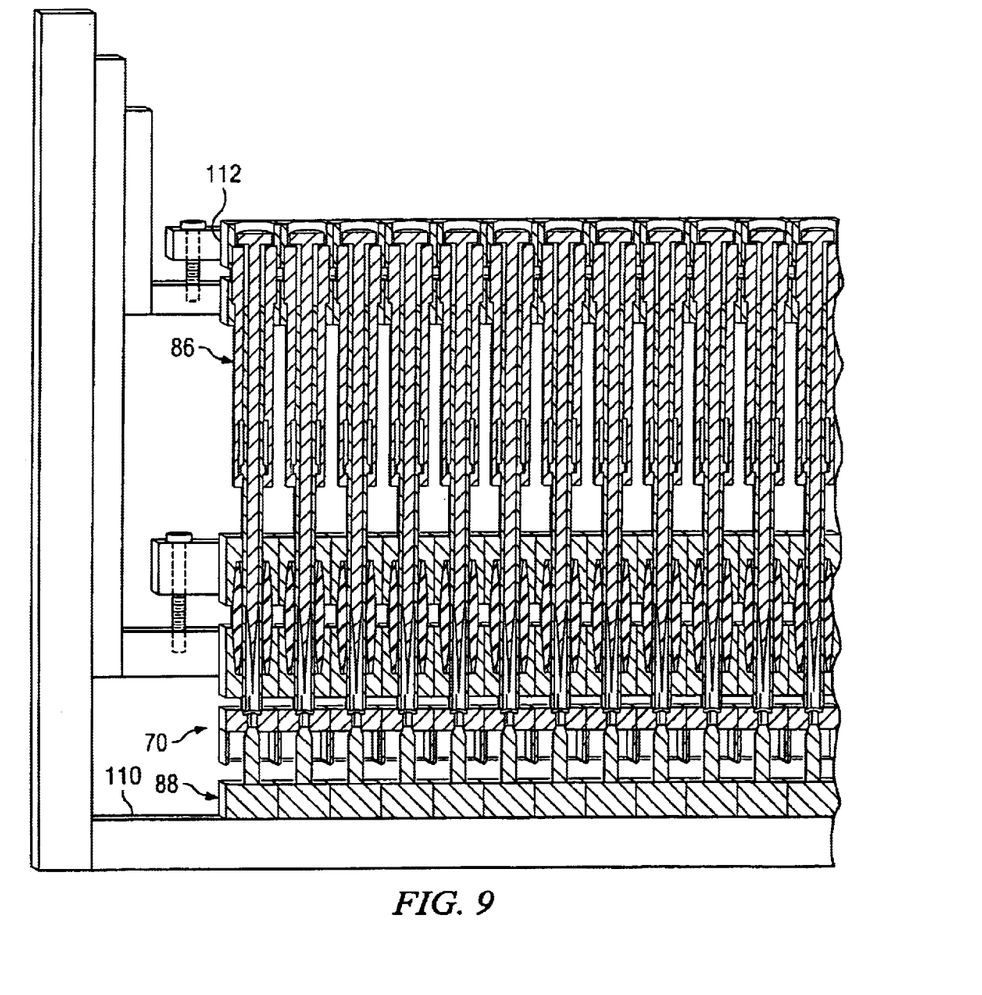
FIG. 9 is a sectioned schematic view of a tray substrate shown up-side-down between a lower frame containing a bank of support assemblies and an upper frame containing a corresponding bank of molding assemblies.
Figure 10:
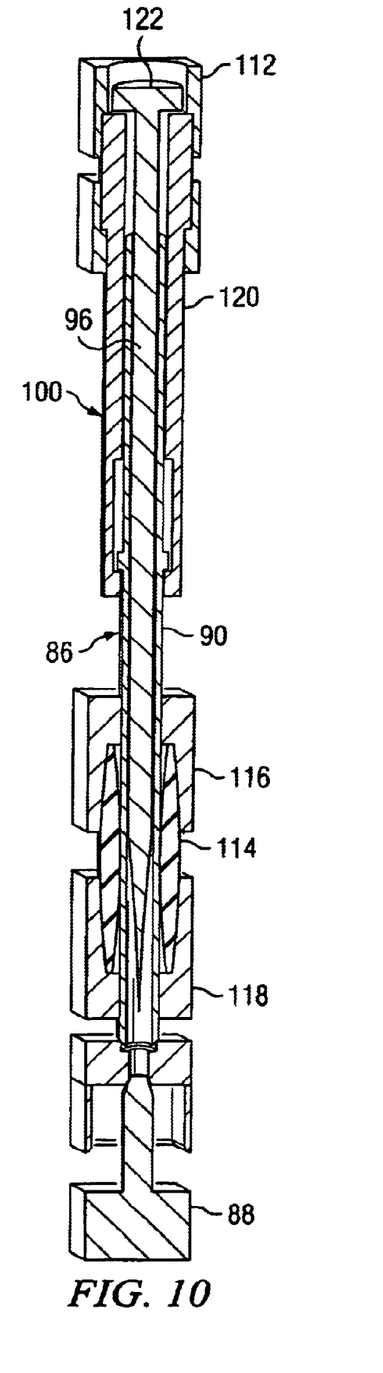
FIGS. 10 and 11 show the single-well details of the components of the molding and support assemblies according to one embodiment of the invention.
Figure 11:
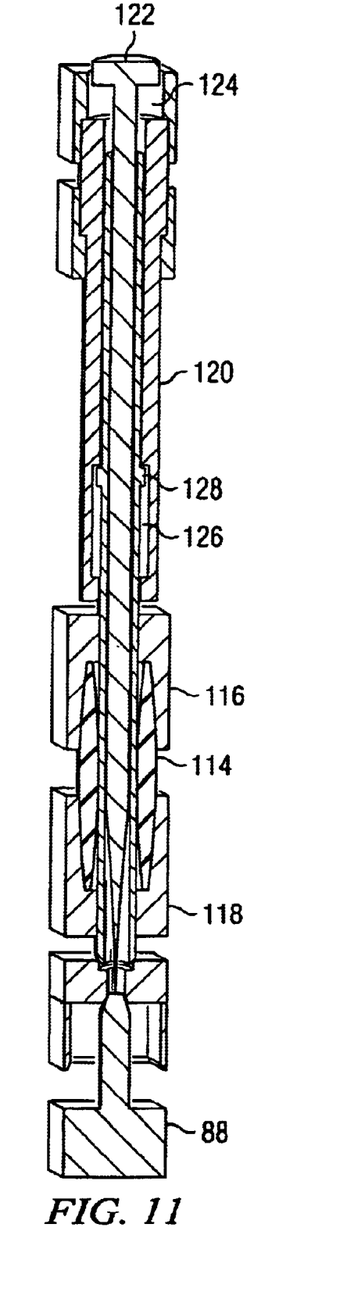

As one skilled in the art would readily appreciate, the manufacture of the multi-well tray of the invention can be automated by mounting a bank of molding assemblies 86 on a top frame and a bank of support assemblies 88 on a bottom frame in alignment with each well in the tray substrate 70, and by providing robotic equipment to perform the molding operation described above while the tray substrate is held up-side-down between the two frames. FIG. 9 is a sectioned schematic view of one embodiment of this type of apparatus. The tray substrate 70 is shown up-side-down sandwiched between a lower frame 110 containing a bank of support assemblies 88 and an upper frame 112 containing a corresponding bank of molding assemblies 86. As seen in clearer detail in the single-well views of FIGS. 10 and 11, each molding assembly 86 is mounted within a resilient grommet 114 that is pressed by two collinear casings 116,118 to provide frictional coupling with the outer sleeve 90 of the molding assembly. When the casings 116,118 are pulled apart, the pressure on the sleeve 90 is released and it can be extracted therefrom for replacement. The motion of the inner plunger 96 of the molding assembly relative to the outer sleeve 90 is controlled by a tube 120 that is slidably mounted over the sleeve 90 in the frame 112. The inner plunger 96 includes a stop 122 that butts against the tube 120, so that the free-fall (gravitational) downward motion of the plunger 96 is limited by the vertical position of the tube 120 relative to the sleeve 90. When the tube 120 is in a raised position, as seen in FIG. 10, the plunger 96 is also correspondingly raised by the stop 122. When the tube 120 is lowered, as seen in FIG. 11, the plunger 96 is free to fall by the same amount, as measured by the opening 124 created by lowering the tube 120 with respect to the sleeve 90. Thus, the plunger 96 is free to fall according to the invention to mold the aperture 54 in the polymeric plug being manufactured in the tray substrate 70. A travel cavity 126 and a corresponding travel stop 128 are provided in the tube 120 and the sleeve 90, respectively, to limit the relative motion of the two components as needed to accomplish the objectives of the invention.

Figure 12:
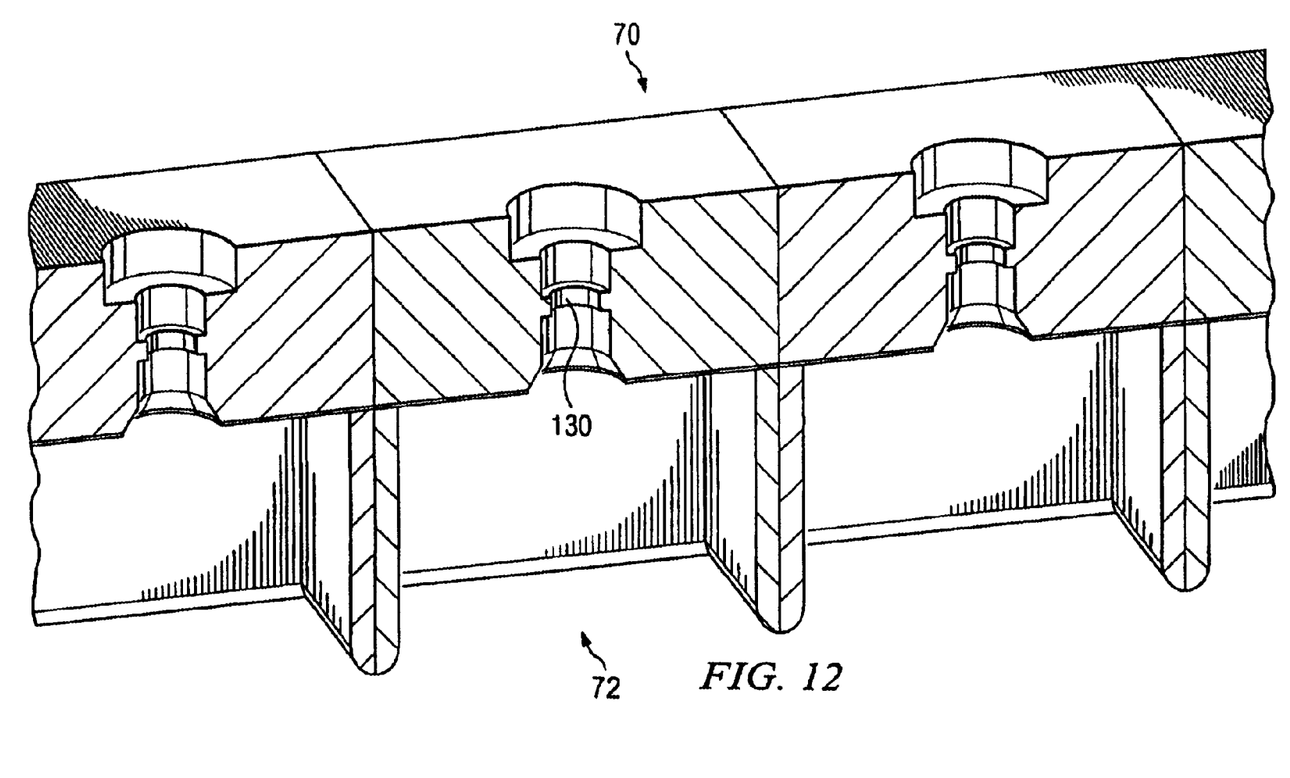
FIG. 12 illustrates an alternative embodiment of a multi-well tray manufactured according to the invention, wherein a protrusion is provided to firmly anchor each electrode plug within its seat in the tray.
Figure 13A:
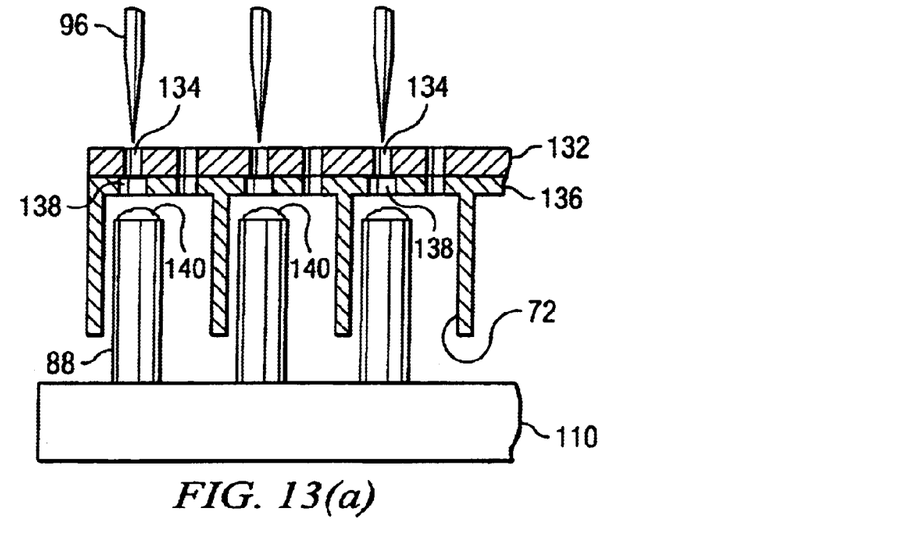
Figure 13B:
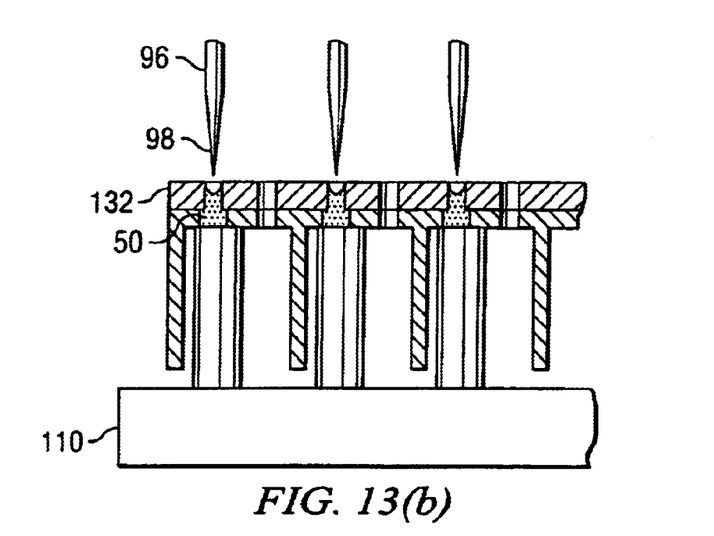
Figure 13C:
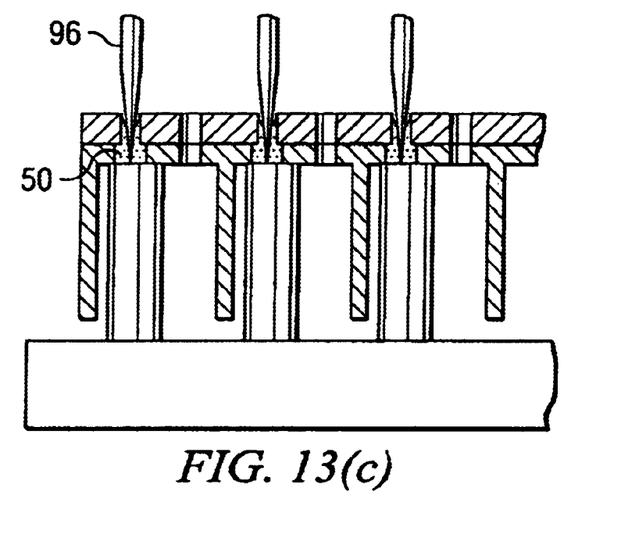
Figure 13D:
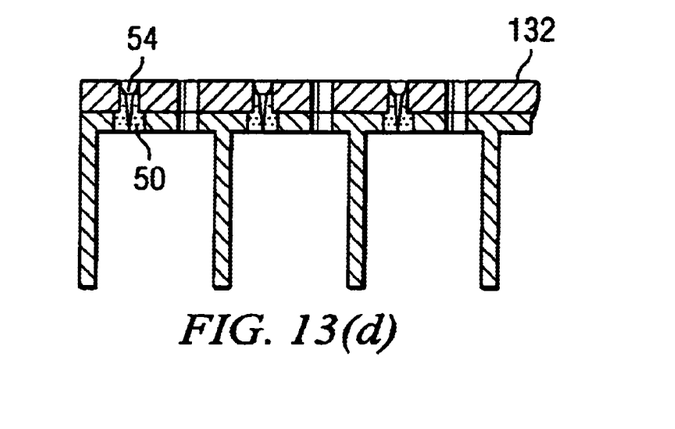

According to another embodiment of the invention illustrated in FIG. 12, the retention of each polymeric plug 50 within the perforation 74 of the tray substrate 70 is improved by providing an inner retaining protrusion 130 that firmly anchors the cured plug to the tray. Another approach to enhancing the bonding of the polymeric plugs to the supporting structure could lie in forming them within a cavity in the same material. Thus, for example, a perforated PDMS sheet could be combined with a rigid support structure, and a PDMS plug could be made according to the invention in each hole in the sheet. FIGS. 13(a)–(d) illustrate schematically in cross-section a PDMS sheet 132 with multiple holes 134 overlaying a rigid support layer 136 with matching holes 138 that correspond to the perforations 74 in the tray substrate 70 of FIGS. 6–12. An appropriate quantity 140 of PDMS is deposited on top of each finger 88 and squeezed into each pair of holes 134,138 to form an uncured plug 50, as illustrated in FIG. 13(b). Pointed plungers 96 are then lowered, as detailed above, to pierce the plugs 50 with their tips 98 and form conforming electrode apertures 54. The PDMS is cured in conventional manner and, finally, the plungers 96 are removed, leaving solid PDMS plugs 50 cured within the PDMS sheet 132 for greater adhesion. The multi-well structure illustrated in FIG. 13(d) is then inverted and used in conventional manner.

Thus, it has been demonstrated that multi-well trays manufactured according to the invention are suitable for use in parallel-testing patch-clamp systems wherein each chamber is used sequentially to test series of cells with a variety of perfusion solutions. Multiple perfusion chambers equipped with the electrode trays of the invention can be operated independently and in parallel with greatly reduced manual operation. Therefore, series of successive tests can be carried out rapidly and precisely.

Various changes in the details, steps and components that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and procedures.

We claim:

1. A patch-clamp electrode structure comprising:

a support structure defining a cavity;

a polymeric plug in the cavity; and an aperture through the polymeric plug;

wherein said aperture conforms to a pointed tip of a patch-clamp micropipette; and wherein said cavity includes a retaining protrusion for anchoring the polymeric plug.

2. A multi-well tray manufactured according to the method comprising the following steps:

providing a tray with a plurality of wells and an electrode perforation in each well;

placing a predetermined amount of uncured polymeric material in the electrode perforation in each well to form a layer over a support surface;

piercing said layer in each well with a pointed plunger having a tip conforming to an aperture suitable for forming a high-resistance patch-clamp seal with a biological membrane;

curing the layer of polymeric material to form a solid plug within the electrode perforation; and removing the pointed plunger and the support surface from the plug.

3. A multi-well patch-clamp electrode structure comprising:

a tray with a plurality of wells and an electrode perforation in each well;

a polymeric plug in the electrode perforation of each well; and an aperture through each polymeric plug;

wherein said aperture conforms to a pointed tip of a patch-clamp micropipette.

4. The electrode structure of claim 3, wherein said polymeric plug comprises a cured silicone polymer.

5. The electrode structure of claim 3, wherein said polymeric plug comprises cured poly-dimethylsiloxane.

6. The electrode structure of claim 3, further comprising a layer of polymeric material with a plurality of openings overlaying said electrode perforations; and wherein said polymeric plug extends into said overlaying opening in the layer of polymeric material.

7. The electrode structure of claim 3, wherein said electrode perforation includes a retaining protrusion for anchoring the polymeric plug.

8. The electrode structure of claim 3, wherein said aperture has a diameter of about 0.5–20 microns at a smaller end thereof.

9. The electrode structure of claim 3, wherein said aperture is at least 0.1 mm deep.

* * * * *